US00PP25517P2

(12) United States Plant Patent
Hanna et al.

(10) Patent No.: US PP25,517 P2
(45) Date of Patent: May 5, 2015

(54) GRASS 'TIFT 15'

(50) Latin Name: ***Pennisetum purpureum*×[*Pennisetum glaucum*×(*Pennisetum purpureum*×*Pennisetum squamulatum*)]**
Varietal Denomination: Tift 15

(71) Applicant: University of Georgia Research Foundation, Inc., Athens, GA (US)

(72) Inventors: Wayne W. Hanna, Chula, GA (US); S. Kristine Braman, Griffin, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 160 days.

(21) Appl. No.: 13/986,888

(22) Filed: Jun. 13, 2013

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Pennisetum* 'Tift 15' is provided. The new and distinct variety has high ornamental value, cold tolerance for short periods of time, and disease resistance. The asexually reproduced variety is reliably propagated vegetatively.

1 Drawing Sheet

Latin name of the genus and species of the plant claimed: 'Tift 15' is a tri-specific ornamental *Pennisetum* hybrid of the genus and species *Pennisetum purpureum*×[*Pennisetum glaucum*×(*Pennisetum purpureum*×*Pennisetum squamulatum*)].

Variety denomination: The new *Pennisetum* claimed is of the variety denominated 'Tift 15'.

BACKGROUND OF THE INVENTION

The present invention relates to a new and distinct cultivar of *Pennisetum* herein referred to as 'Tift 15'.

The new *Pennisetum* 'Tift15' is a product of a planned breeding program conducted by the Inventors in Tifton, Ga. The objective of the *Pennisetum* breeding program is to create new plant cultivars with improved commercial qualities. This cultivar is commercially important for its superior ornamental value. These and other qualities are enumerated herein.

Pedigree and history: In 2003, red tetraploid (2n=4x=28) pearl millet (unpatented *Pennisetum glaucum*; designated '04-94') was crossed with SC 1125-2 [a Merkeron napiergrass (unpatented *Pennisetum purpureum;* 2n=4x=28) that had been crossed with PS 262 (unpatented *Pennisetum squamulatum;* 2n=8x=56)]. One vigorous plant, from the 04-94/SC 1125-2 cross, designated '04-26-1,' was selected in 2004. In 2004, 'Princess' napiergrass (U.S. Plant Pat. No. 17,728; 2n=4x=28, female parent) was pollinated with '04-26-1' (unpatented; male parent). The new variety 'Tift 15' was the fifteenth plant selected in 2005 from the 2004 cross. The new variety 'Tift 15' has been tested since 2005.

Asexual reproduction of the new *Pennisetum* 'Tift 15' by vegetative propagation (single stem propagules) in a controlled environment in Tifton, Blairsville, and Griffin, Ga. since 2005, has shown that the unique features of this new *Pennisetum* hybrid are stable and reproduced true to type in successive generations.

SUMMARY OF THE INVENTION

The following traits have been repeatedly observed and represent the characteristics of a new variety *Pennisetum*, 'Tift 15'. The new variety 'Tift 15' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed in Tifton, Blairsville, and Griffin, Ga., and are determined to be the unique characteristics of the new variety 'Tift 15':

1. 'Tift 15' reaches a height of about 70 cm, and a spread of about 160 cm.
2. 'Tift 15' exhibits a vigorous growth habit.
3. 'Tift 15' is pollen and seed sterile.

The new variety *Pennisetum* 'Tift 15' can be compared to its parents, 'Princess' and '04-26-01'.

Plants of the new *Pennisetum* 'Tift 15' differ from its female parent 'Princess' in the following characteristics:

1. The leaf length of the new variety 'Tift 15' is longer than for 'Princess'.
2. The adaxial and abaxial leaf colors of the 'Tift 15' do not have the mottled grey-purple/green colors of 'Princess'.

Plants of the new *Pennisetum* 'Tift 15' differ from its male parent '04-26-1' in the following characteristics:

1. The new variety 'Tift 15' is slightly different from '04-26-1' in adaxial leaf color. The new variety 'Tift 15' is about Greyed-purple RHS 187D, whereas '04-26-1' is about mottled Greyed-purple/green RHS 183B/138A.
2. The new variety 'Tift 15' has a different midrib color. The new variety 'Tift 15' has a midrib color that is about Greyed-purple RHS 187B, while '04-26-1' has a midrib color that is about Red-purple RHS 61C.

The following observations, measurements, and values describe plants grown in Tifton, Blairsville, or Griffin, Ga. In Tables 1-5, the least significant difference (LSD) is set at P≤0.05 probability level. Growth days were included in ratings. Plants were spaced at 2 meter centers. All data are from plants established as single stem propagules in mid-May and rated in September through October, except the data from 2010 and 2011, in which the plants had been overwintered at Tifton, Ga.

The new variety 'Tift 15' was significantly shorter than 'Princess' in two of three tests at Tifton, Ga. and in one test at Griffin, Ga. (Table 1). There was no significant difference in the plant height of the two cultivars at Blairsville, Ga. (Table 1). The canopy diameter was significantly wider for 'Tift 15' than 'Princess' in three of six tests in Tifton, Blairsville, and Griffin, Ga. (Table 2). 'Tift 15' has an attractive reddish/purple color and was equal to 'Princess' in three of six tests and significantly better color in three tests (Table 3). The new variety 'Tift 15' is not disease-susceptible to *Helminthosporium* leaf spot, whereas 'Princess' is susceptible to this disease (Table 4). Leaves of 'Tift 15' are significantly longer, but similar in width, and leaf area compared to the leaves of 'Princess' (Table 5). There was no significant difference in culm-leaf angle between 'Tift 15' and 'Princess'.

TABLE 1

Plant heights (cm) of two ornamental *Pennisetum* grasses planted at three locations in Georgia.

| | Tifton | | | Blairsville | | Griffin |
|---|---|---|---|---|---|---|
| | 2009 | 2010 | 2011 | 2010 | 2011 | 2009 |
| Growth days | 153 d | 150 d | 183 d | 145 d | 160 d | 141 d |
| 'Tift 15' | 63 | 80 | 61 | 85 | 90 | 110 |
| 'Princess' | 82 | 96 | 64 | 94 | 103 | 184 |
| LSD | 7 | 15 | NS | NS | NS | 21 |

In Table 1, plant heights were measured from ground level to top of plant canopy. All height measurements are in cm. At Tifton, Ga., 'Tift 15' and 'Princess' were planted on May 9, 2009, May 9, 2010, and May 12, 2011, with measurements taken on Oct. 12, 2009, Sep. 29, 2010, and Oct. 18, 2011. At Blairsville, Ga., 'Tift 15' and 'Princess' were planted on May 14, 2009, May 11, 2010, and May 1, 2011, with measurements made on Oct. 8, 2009, Oct. 6, 2010 and Oct. 10, 2011, respectively. At Griffin, Ga., 'Tift 15' and 'Princess' were planted on May 14, 2009, with measurements taken on Oct. 2, 2009.

TABLE 2

Canopy diameter (cm) of individual plant of two ornamental *Pennisetum* grasses planted at three locations in Georgia. Plants were spaced on two meter centers.

| | Tifton | | | Blairsville | | Griffin |
|---|---|---|---|---|---|---|
| | 2009 | 2010 | 2011 | 2010 | 2011 | 2009 |
| Growth days | 153 d | 150 d | 183 d | 145 d | 160 d | 141 d |
| 'Tift 15' | 138 | 123 | 133 | 150 | 151 | 164 |
| 'Princess' | 120 | 120 | 135 | 138 | 130 | 190 |
| LSD | 7 | NS | NS | NS | 12 | 28 |

Plant canopy measurements, as shown in Table 2, represent the average diameters measured at the estimated widest and narrowest portions of a single plant canopy. Measurements are in cm. At Tifton, Ga., 'Tift 15' and 'Princess' were planted on May 9, 2009, May 9, 2010, and May 12, 2011, with measurements taken on Oct. 12, 2009, Sep. 29, 2010, and Oct. 18, 2011. At Blairsville, Ga., 'Tift 15' and 'Princess' were planted on May 11, 2010 and May 1, 2011, with measurements made on Oct. 6, 2010 and Oct. 10, 2011. At Griffin, Ga., 'Tift 15' and 'Princess' were planted on May 14, 2009, with measurements taken on Oct. 2, 2009.

TABLE 3

Color ratings on individual plants of two ornamental *Pennisetum* grasses planted at three locations in Georgia. Plants were spaced on two meter centers.

| | Tifton | | | Blairsville | | Griffin |
|---|---|---|---|---|---|---|
| | 2009 | 2010 | 2011 | 2010 | 2011 | 2009 |
| Growth days | 153 d | 150 d | 183 d | 145 d | 160 d | 141 d |
| 'Tift 15' | 7.0 | 7.0 | 7.0 | 7.0 | 7.0 | 7.0 |
| 'Princess' | 7.0 | 3.1 | 6.0 | 5.6 | 5.3 | 7.0 |
| LSD | NS | NS | 0.6 | 0.8 | 0.6 | NS |

Color ratings are measured on a scale of 1 to 9, where 1 represents green and 9 represents dark purple/red. At Tifton, Ga., 'Tift 15' and 'Princess' were planted May 9, 2009, May 9, 2010, and May 12, 2011, with measurements taken on Oct. 12, 2009, Sep. 29, 2010, and Oct. 18, 2011. At Blairsville, Ga., 'Tift 15' and 'Princess' were planted on May 11, 2010 and May 1, 2011, with measurements taken on Oct. 6, 2010 and Oct. 10, 2011. At Griffin, Ga., 'Tift 15' and 'Princess' were planted on May 14, 2009, with measurements taken Oct. 2, 2009.

TABLE 4

*Helminthosporium* leaf spot ratings on two ornamental *Pennisetum* grasses planted at two locations in Georgia.

| | Tifton | | Blairsville | |
|---|---|---|---|---|
| | 2010 | 2011 | 2010 | 2011 |
| Growth days | 150 d | 183 d | 145 d | 160 d |
| 'Tift 15' | 1.0 | 1.0 | 1.0 | 1.0 |
| 'Princess' | 6.6 | 8.0 | 5.0 | 7.6 |
| LSD | 0.1 | 0.0 | 1.2 | 0.2 |

Disease ratings in Table 9 are defined as follows: 1=No disease, 2=1-20%, 3=21-30%, 4=31-40%, 5=41-50%, 6=51-60%, 7=61-70%, 8=71-80%, 9=>80% leaves infected. Symptoms occur in the field during late August and September. At Tifton, Ga., 'Tift 15' and 'Princess' were planted on May 9, 2010 and May 12, 2011, with measurements taken on Sep. 29, 2010 and Oct. 18, 2011. At Blairsville, Ga., 'Tift 15' and 'Princess' were planted on May 11, 2010 and May 1, 2011, with measurements taken on Oct. 6, 2010 and Oct. 10, 2011.

TABLE 5

Leaf characteristics of individual plants of two ornamental *Pennisetum* grasses planted at Tifton, Georgia in 2009. Plants were spaced on two meter centers.

| Entry | Leaf Length (cm) | Leaf Width (mm) | Leaf Area ($cm^2$) | Leaf Angle Culm:Leaf |
|---|---|---|---|---|
| 'Tift 15' | 64 | 34 | 158 | 13 |
| 'Princess' | 49 | 37 | 132 | 13 |
| LSD | 6 | NS | NS | NS |

The leaf length was measured in cm from the leaf collar to the leaf tip of the latest fully extended leaf. The leaf width was measured in mm in the center of the latest fully extended leaf. The leaf area was measured in $cm^2$ using a LiCor area meter using the mean of three leaves per replication. The measured leaf angle was the angle observed between the adaxial leaf angle surface and the culm at the leaf collar on the last fully extended leaf and was measured in degrees. At Tifton, Ga., 'Tift 15' was planted on May 9, 2009, with measurements taken on Sep. 12, 2009.

TABLE 6

Summary of morphological characteristics of two *Pennisetum* grasses.

| Trait | 'Princess' | 'Tift 15' |
|---|---|---|
| Mature plant height | 64-184 cm | 61-110 cm |
| Diameter of plant canopy | 120-190 cm | 123-154 cm |
| Leaf width | 37 mm | 34 mm |
| Leaf length | 49 cm | 64 cm |
| Leaf Area-$cm^2$ | 132 | 158 |
| Leaf Angle (Stem:Leaf) | 13 degrees | 13 degrees |
| Adaxial leaf surface trichomes | None | Few, 1 mm on both side of midrib |
| Abaxial leaf surface trichomes | None | None |
| Leaf blade margin trichome length | <0.1 m | Less than 0.1 mm long |
| Leaf collar trichome length | 1 mm | Dense, 2 mm long |
| Leaf blade edge at collar | 3 mm long for 3.5 cm from collar | Sparse at base (5 mm long) for 6 cm from collar |
| Trichome | | |
| Sheath trichomes | Less than 1.0 mm | None |
| Adaxial leaf color | Mottled Greyed-purple/Green 187D/137B | Greyed-purple 187D |
| Abaxial leaf color | Mottled Greyed-purple/Green 187D/137B | Greyed-purple 187A |
| Midrib color | Greyed-purple 187C | Greyed-purple 187B |
| Inflorescences on Dec. 21, 2009 | None | None |
| *Helminthosporium* leaf spot on mature plants | Yes | None |

In summary, 'Tilft 15' is either equal in height or significantly shorter and is either equal in color or has significantly better color compared to 'Princess.' 'Tift 15' has better disease resistance than 'Princess.' 'Tift 15' has longer leaves than 'Princess.'

BRIEF DESCRIPTION OF THE FIGURES

The accompanying colored photographs illustrate the overall appearance and distinct characteristics of the new variety of *Pennisetum* 'Tift 15.' The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

FIG. 1 is a photograph of the new variety *Pennisetum* 'Tift 15.'

BOTANICAL DESCRIPTION

The new variety 'Tift 15' is a perennial at Tifton, Ga. (USDA Zone 8a). The new variety 'Tift 15' survived at approximately −6° C. for one night and 21 nights below 0° C. in the field during the 2009/2010 winter at Tifton. It has survived the winter temperatures (−7° C. for one night and 24 nights below 0° C. in the field during 2010/2011) in Tifton. It has not survived the winter temperatures at Griffin, Ga. (USDA Zone 7b) or in the mountains of Blairsville, Ga. (USDA Zone 6b). Because of its vigor, it can effectively be used as an annual where it will not survive freezing temperatures in the winter.

All data are from plants established as single stem propagules in mid-May, and rated in September through October, except the 2010 and 2011 data are from plants that over-wintered at Tifton. Plants were spaced at 2 meter centers.

Plant:

*Mature plant height*.—Approximately 61-110 cm.

*Diameter of plant canopy*.—Approximately 123-154 cm.

Leaf:

*Leaf width*.—Approximately 34 mm.

*Leaf length*.—Approximately 64 mm.

*Adaxial leaf surface trichomes*.—Few, 1 mm on both sides of midribs.

*Abaxial leaf surface trichomes*.—None.

*Leaf blade margin trichome length*.—Less than 0.1 mm long.

*Leaf collar trichome length*.—Dense, 2 mm long.

*Leaf blade edge at collar trichome*.—Sparse at base (5 mm long) for 6 cm from collar.

*Sheath trichomes*.—None.

*Adaxial leaf color*.—About Greyed-purple RHS 187D.

*Abaxial leaf color*.—About Greyed-purple RHS 187A.

*Midrib color*.—About Greyed-purple RHS 187B.

*Helminthosporium leaf spot on mature plants*.—None.

*Inflorescence*.—None.

Culm:

What is claimed is:

1. A new and distinct variety of the *Pennisetum* plant named 'Tift 15', substantially as illustrated and described herein.

* * * * *

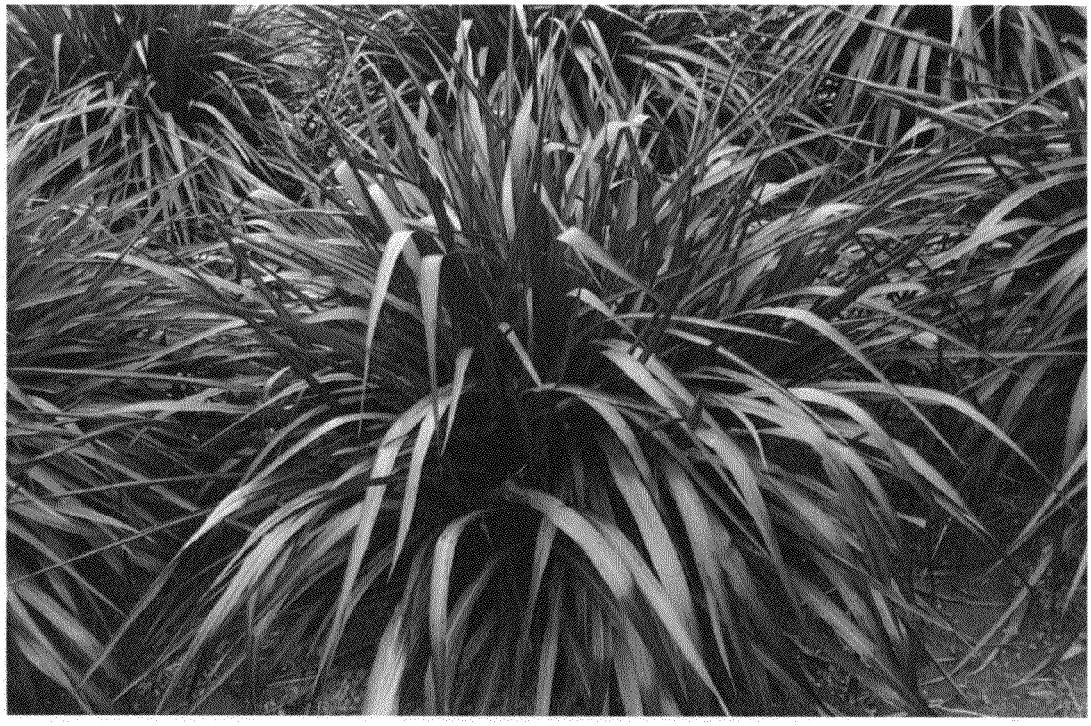

UNITED STATES PATENT AND TRADEMARK OFFICE

CERTIFICATE OF CORRECTION

PATENT NO. : PP25,517 P2
APPLICATION NO. : 13/986888
DATED : May 5, 2015
INVENTOR(S) : Hanna et al.

It is certified that error appears in the above-identified patent and that said Letters Patent is hereby corrected as shown below:

On the Title Page:

Item (50) Latin Name: "*Pennisetum purpureum x [Pennisetum glaucum x (Pennisetum purpureum x Pennisetum squamulatum)]*" should read -- *Pennisetum* hybrid --

Signed and Sealed this
Eighth Day of March, 2016

Michelle K. Lee

Michelle K. Lee
*Director of the United States Patent and Trademark Office*